(12) United States Patent
Hershberger

(10) Patent No.: US 8,986,391 B2
(45) Date of Patent: *Mar. 24, 2015

(54) LATENT MOBILE BEARING FOR PROSTHETIC DEVICE

(71) Applicant: Biomet Manufacturing, LLC, Warsaw, IN (US)

(72) Inventor: Troy W. Hershberger, Winona Lake, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 34 days.

This patent is subject to a terminal disclaimer.

(21) Appl. No.: 13/674,540

(22) Filed: Nov. 12, 2012

(65) Prior Publication Data

US 2013/0173009 A1   Jul. 4, 2013

Related U.S. Application Data

(62) Division of application No. 12/708,755, filed on Feb. 19, 2010, now Pat. No. 8,308,808.

(51) Int. Cl.
*A61F 2/38* (2006.01)
*A61F 2/30* (2006.01)

(52) U.S. Cl.
CPC .................. *A61F 2/38* (2013.01); *A61F 2/3868* (2013.01); *A61F 2002/30062* (2013.01); *A61F 2002/3038* (2013.01); *A61F 2002/30492* (2013.01); *A61F 2210/0004* (2013.01); *A61F 2220/0025* (2013.01); *A61F 2220/0033* (2013.01)
USPC ....................................................... 623/20.29

(58) Field of Classification Search
CPC ........................ A61F 2/38; A61F 2002/30062
USPC ............ 623/20.29, 20.14–20.28, 20.3–20.33, 623/19.11–19.14, 20.11–20.13
See application file for complete search history.

(56) References Cited

U.S. PATENT DOCUMENTS

| 3,728,742 A | 4/1973 | Averill et al. |
| 3,748,662 A | 7/1973 | Helfet |
| 3,774,244 A | 11/1973 | Walker |

(Continued)

FOREIGN PATENT DOCUMENTS

| DE | 2802568 A1 | 7/1979 |
| DE | 3529894 A1 | 3/1987 |

(Continued)

OTHER PUBLICATIONS

"AGC, Total Knee System, Intramedullary with Distractor Surgical Technique," brochure, Biomet, Inc. Jan. 1989.

(Continued)

*Primary Examiner* — Alvin Stewart
(74) *Attorney, Agent, or Firm* — Harness, Dickey

(57) ABSTRACT

A prosthetic device for an anatomical feature includes a prosthetic member able to be fixed to the anatomical feature. The device also includes a bearing including a bearing surface able to support an articulating surface for articulation thereon. Additionally, the device includes a bearing restraining member that limits movement of the bearing relative to the prosthetic member at a first time. The bearing restraining member also allows for increased movement of the bearing relative to the prosthetic member at a second time without surgical intervention.

19 Claims, 5 Drawing Sheets

(56) References Cited

U.S. PATENT DOCUMENTS

| | | |
|---|---|---|
| 3,869,729 A | 3/1975 | Attenborough |
| 3,958,278 A | 5/1976 | Lee et al. |
| 3,964,106 A | 6/1976 | Hutter, Jr. et al. |
| 3,996,624 A | 12/1976 | Noiles |
| 4,081,866 A | 4/1978 | Upshaw et al. |
| 4,085,466 A | 4/1978 | Goodfellow et al. |
| 4,094,017 A | 6/1978 | Matthews et al. |
| 4,136,405 A | 1/1979 | Pastrick et al. |
| 4,205,400 A | 6/1980 | Shen et al. |
| 4,207,627 A | 6/1980 | Cloutier |
| 4,209,861 A | 7/1980 | Walker et al. |
| 4,213,209 A | 7/1980 | Insall et al. |
| 4,215,439 A | 8/1980 | Gold et al. |
| 4,216,549 A | 8/1980 | Hillberry et al. |
| 4,219,893 A | 9/1980 | Noiles |
| 4,224,696 A | 9/1980 | Murray et al. |
| 4,224,697 A | 9/1980 | Murray et al. |
| 4,242,759 A | 1/1981 | White |
| 4,249,270 A | 2/1981 | Bahler et al. |
| 4,257,129 A | 3/1981 | Volz |
| 4,285,070 A | 8/1981 | Averill |
| 4,298,992 A | 11/1981 | Burstein et al. |
| 4,301,553 A | 11/1981 | Noiles |
| 4,309,778 A | 1/1982 | Buechel et al. |
| 4,340,978 A | 7/1982 | Buechel et al. |
| 4,462,120 A | 7/1984 | Rambert et al. |
| 4,470,158 A | 9/1984 | Pappas et al. |
| 4,538,305 A | 9/1985 | Engelbrecht et al. |
| 4,568,348 A | 2/1986 | Johnson et al. |
| 4,586,933 A | 5/1986 | Shoji et al. |
| 4,634,444 A | 1/1987 | Noiles |
| 4,637,382 A | 1/1987 | Walker |
| 4,673,407 A | 6/1987 | Martin |
| 4,711,639 A | 12/1987 | Grundei |
| 4,714,474 A | 12/1987 | Brooks, Jr. et al. |
| 4,728,332 A | 3/1988 | Albrektsson |
| 4,790,853 A | 12/1988 | Engelbrecht et al. |
| 4,808,185 A | 2/1989 | Penenberg et al. |
| 4,822,362 A | 4/1989 | Walker et al. |
| 4,822,365 A | 4/1989 | Walker et al. |
| 4,865,607 A | 9/1989 | Witzel et al. |
| 4,883,488 A | 11/1989 | Bloebaum et al. |
| 4,888,021 A | 12/1989 | Forte et al. |
| 4,892,547 A | 1/1990 | Brown |
| 4,911,721 A | 3/1990 | Andergaten 3 et al. |
| 4,950,297 A | 8/1990 | Elloy et al. |
| 4,950,298 A | 8/1990 | Gustilo et al. |
| 4,959,071 A | 9/1990 | Brown et al. |
| 4,997,445 A | 3/1991 | Hodorek |
| 5,007,933 A | 4/1991 | Sidebotham et al. |
| 5,011,496 A | 4/1991 | Forte et al. |
| 5,037,439 A | 8/1991 | Albrektsson et al. |
| 5,047,057 A | 9/1991 | Lawes |
| 5,064,437 A | 11/1991 | Stock et al. |
| 5,071,438 A | 12/1991 | Jones et al. |
| 5,080,675 A | 1/1992 | Lawes et al. |
| 5,092,895 A | 3/1992 | Albrektsson et al. |
| 5,116,375 A | 5/1992 | Hofmann |
| 5,116,376 A | 5/1992 | May |
| 5,133,758 A | 7/1992 | Hollister |
| 5,139,521 A | 8/1992 | Schelhas |
| 5,147,405 A | 9/1992 | Van Zile et al. |
| 5,147,406 A | 9/1992 | Houston et al. |
| 5,171,283 A | 12/1992 | Pappas et al. |
| 5,176,710 A | 1/1993 | Hahn et al. |
| 5,181,925 A | 1/1993 | Houston et al. |
| 5,197,987 A | 3/1993 | Koch et al. |
| 5,201,881 A | 4/1993 | Evans |
| 5,219,362 A | 6/1993 | Tuke et al. |
| 5,226,916 A | 7/1993 | Goodfellow et al. |
| 5,236,461 A | 8/1993 | Forte |
| 5,271,747 A | 12/1993 | Wagner et al. |
| 5,282,868 A | 2/1994 | Bahler |
| 5,282,870 A | 2/1994 | Moser et al. |
| 5,314,482 A | 5/1994 | Goodfellow et al. |
| 5,314,483 A | 5/1994 | Wehrli et al. |
| 5,330,532 A | 7/1994 | Ranawat |
| 5,330,533 A | 7/1994 | Walker et al. |
| 5,330,534 A | 7/1994 | Herrington et al. |
| 5,358,527 A | 10/1994 | Forte |
| 5,358,529 A | 10/1994 | Davidson |
| 5,358,530 A | 10/1994 | Hodorek |
| 5,358,531 A | 10/1994 | Goodfellow et al. |
| 5,370,699 A | 12/1994 | Hood et al. |
| 5,370,700 A | 12/1994 | Sarkisian et al. |
| 5,370,701 A | 12/1994 | Finn |
| 5,387,240 A | 2/1995 | Pottenger et al. |
| 5,395,401 A | 3/1995 | Bahler |
| 5,405,394 A | 4/1995 | Davidson |
| 5,405,395 A | 4/1995 | Coates |
| 5,405,396 A | 4/1995 | Heldreth et al. |
| 5,413,604 A | 5/1995 | Hodge |
| 5,413,608 A | 5/1995 | Keller |
| 5,466,530 A | 11/1995 | England et al. |
| 5,480,446 A | 1/1996 | Goodfellow et al. |
| 5,514,183 A | 5/1996 | Epstein et al. |
| 5,549,686 A | 8/1996 | Johnson et al. |
| 5,549,689 A | 8/1996 | Epstein et al. |
| 5,549,690 A | 8/1996 | Hollister et al. |
| 5,556,432 A | 9/1996 | Kubein-Meesenburg et al. |
| 5,571,197 A | 11/1996 | Insall |
| 5,609,639 A | 3/1997 | Walker et al. |
| 5,609,643 A | 3/1997 | Colleran et al. |
| 5,609,645 A | 3/1997 | Vinciguerra |
| 5,639,279 A | 6/1997 | Burkinshaw et al. |
| 5,641,323 A | 6/1997 | Caldarise |
| 5,658,342 A | 8/1997 | Draganich et al. |
| 5,658,344 A | 8/1997 | Hurlburt |
| 5,662,158 A | 9/1997 | Caldarise |
| 5,683,467 A | 11/1997 | Pappas |
| 5,683,468 A | 11/1997 | Pappas |
| 5,702,458 A | 12/1997 | Burstein et al. |
| 5,702,466 A | 12/1997 | Pappas et al. |
| 5,725,584 A | 3/1998 | Walker et al. |
| 5,755,801 A | 5/1998 | Walker et al. |
| 5,755,802 A | 5/1998 | Gerber |
| 5,755,804 A | 5/1998 | Schmotzer et al. |
| 5,800,552 A | 9/1998 | Forte |
| 5,824,096 A | 10/1998 | Pappas et al. |
| 5,824,100 A | 10/1998 | Kester et al. |
| 5,824,102 A | 10/1998 | Buscayret |
| 5,824,103 A | 10/1998 | Williams |
| 5,871,542 A | 2/1999 | Goodfellow et al. |
| 5,871,545 A | 2/1999 | Goodfellow et al. |
| 5,871,546 A | 2/1999 | Colleran et al. |
| 5,879,387 A | 3/1999 | Jones et al. |
| 5,879,392 A | 3/1999 | McMinn |
| 5,879,394 A | 3/1999 | Ashby et al. |
| 5,906,643 A | 5/1999 | Walker |
| 5,997,577 A | 12/1999 | Herrington et al. |
| 6,004,352 A | 12/1999 | Buni |
| 6,019,794 A | 2/2000 | Walker |
| 6,039,764 A | 3/2000 | Pottenger et al. |
| 6,068,658 A | 5/2000 | Insall et al. |
| 6,080,195 A | 6/2000 | Colleran et al. |
| 6,090,144 A | 7/2000 | Letot et al. |
| 6,099,570 A | 8/2000 | Livet et al. |
| 6,117,175 A | 9/2000 | Bosredon |
| 6,123,729 A | 9/2000 | Insall et al. |
| 6,152,960 A | 11/2000 | Pappas |
| 6,162,254 A | 12/2000 | Timoteo |
| 6,165,223 A | 12/2000 | Metzger et al. |
| 6,203,576 B1 | 3/2001 | Afriat et al. |
| 6,210,444 B1 | 4/2001 | Webster et al. |
| 6,210,445 B1 | 4/2001 | Zawadzki |
| 6,217,618 B1 | 4/2001 | Hileman |
| 6,296,666 B1 | 10/2001 | Gardner |
| 6,413,279 B1 | 7/2002 | Metzger et al. |
| 6,485,519 B2 | 11/2002 | Meyers et al. |
| 6,660,039 B1 | 12/2003 | Evans et al. |
| 6,923,833 B2 | 8/2005 | Wasielewski |
| 6,972,039 B2 | 12/2005 | Metzger et al. |
| 6,986,791 B1 | 1/2006 | Metzger |
| 7,871,442 B2 | 1/2011 | Servidio |

(56) References Cited

U.S. PATENT DOCUMENTS

| | | | |
|---|---|---|---|
| 8,308,808 B2* | 11/2012 | Hershberger | 623/20.29 |
| 2005/0107886 A1 | 5/2005 | Crabtree et al. | |
| 2005/0216091 A1 | 9/2005 | Wasielewski | |
| 2007/0100463 A1 | 5/2007 | Aram et al. | |
| 2007/0162143 A1 | 7/2007 | Wasielewski | |
| 2007/0162144 A1 | 7/2007 | Wasielewski | |
| 2008/0091272 A1 | 4/2008 | Aram et al. | |
| 2009/0125116 A1 | 5/2009 | Crabtree et al. | |
| 2009/0318976 A1* | 12/2009 | Gabriel et al. | 606/283 |
| 2011/0208316 A1* | 8/2011 | Hershberger | 623/20.29 |
| 2013/0173009 A1* | 7/2013 | Hershberger | 623/20.29 |

FOREIGN PATENT DOCUMENTS

| | | |
|---|---|---|
| DE | 4009360 A1 | 8/1991 |
| EP | 0186471 A2 | 7/1986 |
| EP | 0327297 A2 | 8/1989 |
| EP | 0346183 A1 | 12/1989 |
| EP | 0349173 A1 | 1/1990 |
| EP | 0381352 A1 | 8/1990 |
| EP | 0442330 A2 | 8/1991 |
| EP | 0498586 A1 | 8/1992 |
| EP | 0510178 A1 | 10/1992 |
| EP | 0510299 A1 | 10/1992 |
| EP | 0519873 A2 | 12/1992 |
| EP | 0592750 A1 | 4/1994 |
| EP | 0627203 A2 | 12/1994 |
| EP | 653927 A1 | 5/1995 |
| EP | 0970667 A1 | 1/2000 |
| FR | 2663536 A1 | 12/1991 |
| FR | 2685632 A1 | 7/1993 |
| FR | 2758456 A1 | 7/1998 |
| GB | 1534263 A | 11/1978 |
| GB | 2219942 A | 12/1989 |
| GB | 2296443 A | 7/1996 |
| GB | 2313314 A | 11/1997 |
| WO | WO-9203108 A1 | 3/1992 |
| WO | WO-9208424 A1 | 5/1992 |
| WO | WO-9426212 A1 | 11/1994 |
| WO | WO-9603097 A1 | 2/1996 |
| WO | WO-9624311 A1 | 8/1996 |
| WO | WO-9802116 A1 | 1/1998 |

OTHER PUBLICATIONS

"AGC, Total Knee System, Surgical Overview featuring Accu-Line TM Knee Instrumentation," brochure, Biomet, Inc. Jun. 1991.

"AGC, Total Knee System, Tradition Series," brochure, Biomet, Inc. Jun. 1995.

"AGC, Total Knee System, Unicondylar Surgical Overview," brochure, Biomet, Inc. Jan. 1989.

"Maxim, The Complete Knee System," brochure, Biomet, Inc. Jun. 1995.

"Regenerex® Tibial Cone Augment, Surgical Technique Addendum to the Vanguard® SSK Revision System," brochure. Biomet® Orthopedics. (2009) pp. 1-8 (12 sheets).

"Signature™ Personalized Patient Care, Surgical Technique Addendum to the Vanguard Knee System" brochure. Biomet® Orthopedics, Inc. (2009) pp. 1-8.

"The Oxford® Partial Knee—Surgical Technique" Biomet Orthopedics, 2009.

"The Profix Total Knee System," brochure/advertisement. Smith & Nephew, 1999, 2 sheets.

"Trac Mobile Bearing Knee System, Two Radius Area Contact Posterior Stabilized Mobile Bearing Knee System Surgical Technique" brochure. (1999) 32 sheets.

"Vanguard Complete Knee System, Cruciate Retaining," brochure (6 pages) 2007. Biomet Orthopedics, Inc.

"Vanguard Complete Knee System, System Summary," brochure, (4 sheets) 2007. Biomet Orthopedics, Inc.

"Vanguard™ Complete Knee System SSK Revision System," brochure. Biomet Orthopedics, Inc. 2007.

"Vanguard® PFR Partial Knee Patellofemoral Replacement System," Surgical Technique brochure. Biomet Orthopaedics, (2010) pp. 1-25.

Aglietti, P., et al., "Total Knee Replacement—Problems Related to the Posterior Cruciate Ligament and Fixed Versus Mobile Bearings," European Federation of National Associations of Orthopaedics and Traumatology, (1997) pp. 15-24.

Churchill, D. L., et al. "The Transepicondylar Axis Approximates the Optimal Flexion Axis of the Knee," Clinical Orthopaedics and Related Research (Nov. 1998) No. 356, pp. 111-118.

Kocmond, J. H., et al. "Stability and Range of Motion of Insall-Burstein Condylar Prostheses", The Journal of Arthroplasty, (1995) vol. 10, No. 3, pp. 383-388.

Kurosawa, H., et al., "Geometry and Motion of the Knee for Implant and Orthotic Design," J. Biomechanics (1985) vol. 18, No. 7, pp. 487-499.

Markolf, Keith L., et al. "The Role of Joint Load in Knee Stability," Journal of Bone and Joint Surgery, Incorporated (Apr. 1981) vol. 63-A, No. 4 pp. 570-585.

Menchetti, Paolo, M., et al. "Mechanical Evaluation of Mobile Bearing Knees." The American Journal of Knee Surgery, (Spring 1997) vol. 10, No. 2, pp. 73-82.

Microplasty™ minimally invasive knee instruments brochure, Surgical Technique for the Maxim®, Ascent™ and Vanguard™ Total Knee Systems, Biomet Orthopedics, Inc., Feb. 29, 2004.

Schipplein, O.D., et al. "Interaction Between Active and Passive Knee Stabilizers During Level Walking," Journal of Orthopaedic Research (1991) vol. 9, No. 1, pp. 113-119.

Vanguard™ SSK Revision System—Surgical Technique, Biomet® Orthopedics, 2008.

Vanguard® SSK Revision System, 2009.

Walker, P.S., et al., "Controlling the Motion of Total Knee Replacements using Intercondylar Guide Surfaces," Journal of Orthopedic Research (2000) vol. 18, pp. 48-55.

* cited by examiner

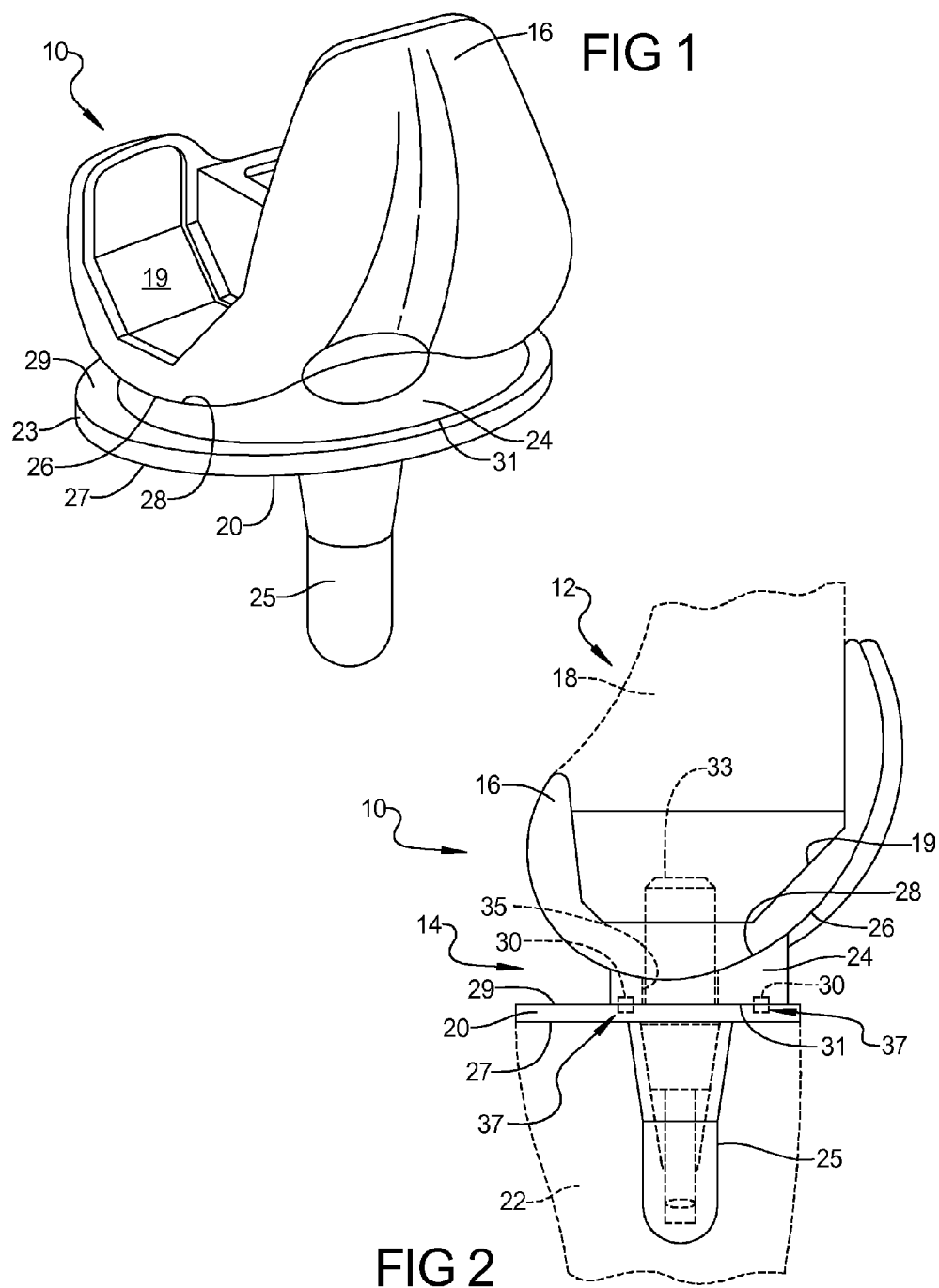

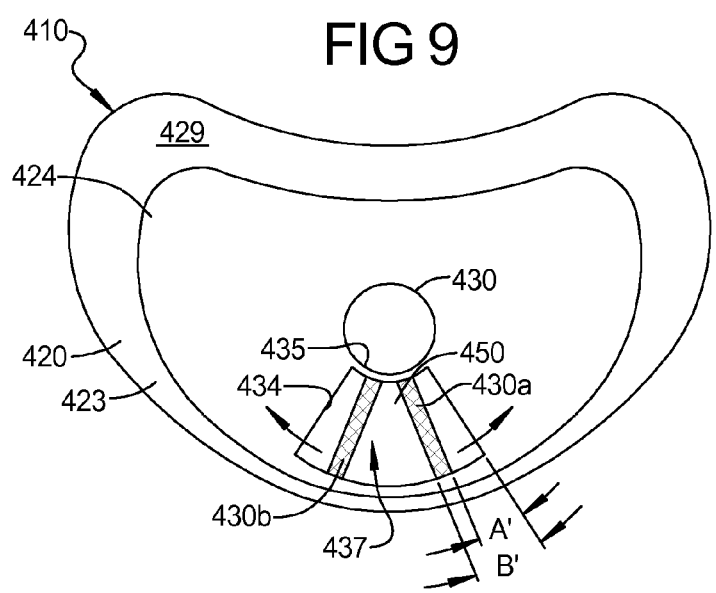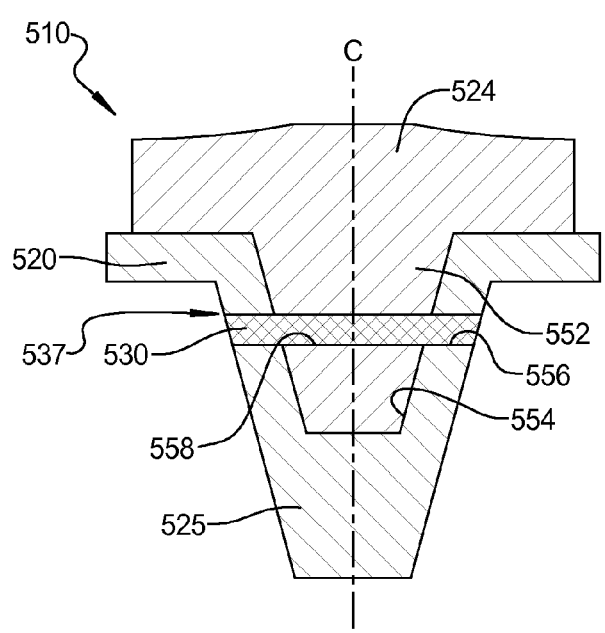

US 8,986,391 B2

LATENT MOBILE BEARING FOR PROSTHETIC DEVICE

CROSS-REFERENCE TO RELATED APPLICATIONS

This application is a divisional of U.S. patent application Ser. No. 12/708,755 filed on Feb. 19, 2012. The entire disclosure of the above application is incorporated herein by reference.

FIELD

The following relates to a prosthetic device and, more particularly, to a latent mobile bearing for a prosthetic device.

BACKGROUND

The statements in this section merely provide background information related to the present disclosure and may not constitute prior art.

Prosthetic joints can reduce pain due to arthritis, deterioration, deformation, and the like, and can improve mobility of the joint. Oftentimes, prosthetic joints can include certain implantable prosthetic members that are fixed to the patient's anatomy. For instance, knee joint prosthetic devices can include a femoral component fixed to the patient's femur and a tibial component fixed to the patient's tibia. Also, the device can include a bearing disposed between the femoral and tibial components. The bearing can be supported by the tibial component, and the bearing can include a bearing surface. An articulating surface of the femoral component can articulate on the bearing surface of the bearing.

In some cases, the bearing can be fixedly coupled to the tibial component. In other cases, the bearing can be moveably coupled to the tibial component. Both types of bearings can be of benefit to the patient for providing mobility of the joint. For some patients, the mobile bearing provides better and more natural movement of the articulating joint.

The following discloses a prosthetic device with a bearing that allows for improved articulation of the joint. The prosthetic device also promotes healing of the anatomical tissue.

SUMMARY

A prosthetic device for an anatomical feature is disclosed. The device includes a prosthetic member able to be fixed to the anatomical feature. The device also includes a bearing including a bearing surface able to support an articulating surface for articulation thereon. Additionally, the device includes a bearing restraining member that limits movement of the bearing relative to the prosthetic member at a first time. The bearing restraining member also allows for increased movement of the bearing relative to the prosthetic member at a second time without surgical intervention.

Also, a method of implanting a prosthetic device for an anatomical feature is disclosed. The method includes implanting a prosthetic member in the anatomical feature. Furthermore, the method includes supporting a bearing with the prosthetic member such that movement of the bearing relative to the prosthetic member is limited at a first time and such that allowable movement of the bearing relative to the prosthetic member is increased at a second time without surgical intervention. Moreover, the method includes supporting an articulating surface with the bearing.

Still further, a knee joint prosthetic device supporting movement between a femur and a tibia of a patient is disclosed. The knee joint prosthetic device includes a tibial prosthetic member that can be implanted on the tibia and a femoral prosthetic member that can be implanted on the femur. The femoral prosthetic member includes an articulating surface. Additionally, the prosthetic device includes a bearing supported by the tibial prosthetic member. The bearing includes a bearing surface able to support the articulating surface for articulation thereon. Moreover, the prosthetic device includes a bearing restraining member that limits linear and rotational movement of the bearing relative to the tibial prosthetic member at a first time. The bearing restraining member also allows for increased linear and rotational movement of the bearing relative to the prosthetic member at a second time without surgical intervention.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1 is a perspective view of an exemplary embodiment of a prosthetic device;

FIG. 2 is a side view of the prosthetic device of FIG. 1;

FIG. 9 is a top view of another exemplary embodiment of a resorbing member of the prosthetic device of FIG. 1; and FIG. 10 is a section view of another exemplary embodiment of a resorbing member of the prosthetic device of FIG. 1.

DETAILED DESCRIPTION

Figure 3:
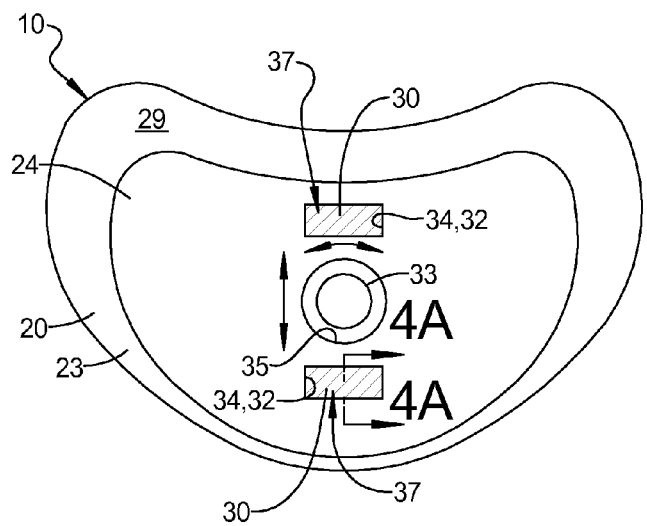
FIG. 3 is a top view of the prosthetic device of FIG. 1.

The following description is merely exemplary in nature and is not intended to limit the present disclosure, application, or uses. It should be understood that throughout the drawings, corresponding reference numerals indicate like or corresponding parts and features.

Referring now to FIGS. 1 and 2, a prosthetic device 10 for an anatomical feature 12 (e.g., a leg) is illustrated according to various exemplary embodiments of the present disclosure. As shown, the prosthetic device 10 can be a prosthetic knee joint 14 (FIG. 2); however, it will be appreciated that the prosthetic device 10 can be of any suitable type for any suitable joint of a patient. Moreover, it will be appreciated that the knee joint 14 can be a cruciate retaining (CR) joint, a posterior stabilized (PS) joint, a fully constrained joint, a hinged knee joint, or any other suitable knee joint 14.

In the embodiments shown, the prosthetic device 10 can include a first prosthetic member 16. The first prosthetic member 16 can be made out of cobalt chromium, titanium or any other suitable biocompatible material. The first prosthetic member 16 can be a first femoral prosthetic member 16 and can be implanted and fixed to an inferior end of a resected femur 18 (FIG. 2). More specifically, the first prosthetic member 16 can include a bone engaging surface 19 that engages the femur 18, and the first prosthetic member 16 can be fixed to the femur 18 via fasteners, bone cement, or any other suitable means. The first prosthetic member 16 can also include one or more articulating surfaces 26 on a side opposite the bone engaging surface 19. For instance, the articulating surfaces 26 can be substantially similar to anatomical medial and lateral condylar surfaces.

Furthermore, the prosthetic device 10 can include a second prosthetic member 20. The second prosthetic member 20 can be made out of cobalt chromium, titanium or any other suitable biocompatible material. The second prosthetic member 20 can be a second tibial prosthetic member 20 and can be implanted and fixed to a superior end of a resected tibia 22 (FIG. 2). The second prosthetic member 20 can include a tray 23 and a post 25. The tray 23 can be relatively flat and can include a bone engaging surface 27 that engages the tibia 22. The tray 23 can also include a superior surface 29 opposite the bone engaging surface 27. The post 25 can be fixed to the tray and can be generally cylindrical. The post 25 can extend inferiorly from the tray 23 and can be received in a corresponding opening in the tibia 22 to fix the second prosthetic member 20 to the tibia 22. The second prosthetic member 20 can also be fixed to the tibia 22 by fasteners, bone cement, or any other suitable means. In addition, the second prosthetic member 20 can include a guide post 33 that is generally cylindrical. The guide post 33 can extend superiorly from the tray 23. It will be appreciated that the guide post 33 can be included, especially, for posterior-stabilized and fully constrained prosthetic knee joint 14; however, it will be appreciated that the guide post 33 may not be necessary for another prosthetic knee joint 14, which nevertheless falls within the scope of the present disclosure.

Moreover, the prosthetic device 10 can include a bearing 24. The bearing 24 can be made out of polyethylene (e.g., ultra high molecular weight polyethylene (UHMWPE)) or any other suitable material. The bearing 24 can include an inferior surface 31 that is supported on and that abuts the superior surface 29 of the tray 23. The bearing 24 can also include a bearing surface 28 opposite the inferior surface 31. The bearing surface 28 can be three-dimensionally and concavely curved. The bearing surface 28 can correspond in shape to the articulating surface 26 of the first prosthetic member 16. As such, the articulating surface 26 can be slidingly supported on the bearing surface 28, and the bearing surface 28 can support the articulating surface 26 for articulation thereon to replicate anatomical movement of the joint 14. Moreover, the bearing 24 can include a through hole 35 that extends between the bearing surface 28 and the inferior surface 31. The guide post 33 can be received within the through hole 35. As shown, the through hole 35 can be larger than the guide post 33 to allow the bearing 24 to move relative to the tray 23 as will be discussed in greater detail.

In addition, the prosthetic device 10 can include one or more bearing restraining mechanisms or members 37. As will be discussed, the bearing restraining members 37 can limit movement of the bearing 24 relative to the tray 23 at a first time (e.g., when the prosthetic device 10 is first implanted). Also, the bearing restraining member 37 can eventually (i.e., at a second time) allow for increased movement of the bearing 24 relative to the tray 23 without surgical intervention.

For instance, the restraining members 37 can initially fix the bearing 24 and tray 23 together such that the relative range of movement (i.e., range of motion, degree of freedom, etc.) is substantially zero millimeters. Then, weeks after surgery, the restraining members 37 can allow the relative range of movement (i.e., the relative range of motion, degree of freedom, etc.) to be greater than zero millimeters. Also, in some embodiments, the restraining members 37 can initially limit the relative range of movement to X millimeters, and the restraining members 37 can eventually allow for a relative range of movement of X+1 millimeters. Still further, in some embodiments, the restraining members 37 can initially allow for a first type of relative movement (e.g., anterior-posterior movement) while limiting a second type of relative movement (e.g., rotational), and the restraining members 37 can eventually allow for both types of relative movement.

In some embodiments, the bearing restraining members 37 can be resorbing members 30 shown schematically in FIG. 2. The resorbing members 30 can be made out of any suitable biologically compatible material that resorbs or partially resorbs in the body. The terms "resorbing," "resorption," "resorb," and other related terms are defined herein as either partial or total loss of volume, strength, hardness, durometer, etc. over time.

The resorbing members 30 can be made out of any suitable resorbing material. This set of materials includes, without limitation, categories of suitable materials such as resorbable polymer materials, resorbable ceramic materials, resorbable metals, biological materials and combinations thereof. Also, the resorbing members 30 can be made out of synthetic materials such as resorbable monomers and polymers, non-limiting examples of which include: certain polyesters, including but not limited to polylactic acid and polyglycolic acid, polycaprolactone, certain polyurethanes, protein or amino acid based polymers, polysaccharides, hyaluronic acid, polyethylene glycol, activated or modified forms of these materials, combinations of these materials, co-polymers and ter-polymers of these materials, and these materials in combination with other materials. Moreover, in some embodiments, the resorbing members 30 can be made out of LACTOSORB®, which is commercially available from Biomet of Warsaw, Ind. and is a co-polymer of polylactic acid and polyglycolic acid. Non-limiting examples of resorbable ceramics include calcium containing ceramics such as certain calcium phosphates, calcium sodium phosphates, calcium sulfates, and combinations thereof. A non-limiting example of a potentially suitable resorbable metal includes magnesium alloys. Non-limiting examples of suitable biological materials may include cellulose, gelatin, autograft tissue, allograft tissue, xenogenic material, and extra cellular matrices (ECMs). Exemplary non-limiting examples of such ECMs include, without limitation, porcine small intestine submucosa (SIS), xenogeneic small intestine submucosa (xSIS), urinary bladder submucosa (UBS), laminated intestinal submucosa, glutaraldehyde-treated bovine pericardium (GLBP), and other acellular collagen containing materials. The resorbing members 30 can be layered, molded, formed, braided, perforated, multilaminated, grafted or otherwise manipulated to achieve the desired properties and dimensions.

The resorbing members 30 can be disposed between the bearing 24 and the second prosthetic member 20 and can at least temporarily couple the bearing 24 to the second prosthetic member 20 so that the bearing 24 can be fixed or immovable relative to the tray 23. As such, the resorbing members 30 can temporarily limit a range of movement of the bearing 24 relative to the second prosthetic member 20. Also, as will be discussed in greater detail below, the resorbing members 30 can resorb (i.e., reduce in size and be resorbed within the patient's body) to allow movement of the bearing 24 relative to the second prosthetic member 20 within an increased range of motion.

Accordingly, as will be discussed, the resorbing members 30 can be strong enough to limit movement of the bearing 24 relative to the second prosthetic member 20. For instance, when the prosthetic device 10 is initially implanted, the resorbing members 30 can substantially fix the bearing 24 to the second prosthetic member 20 to promote healing of soft tissue, etc. Over time, the resorbing members 30 can resorb, and the bearing 24 can move relative to the second prosthetic member 20. This movement of the bearing 24 can allow for improved mobility of the joint 14 as discussed in U.S. Pat. No. 6,972,039, filed Jul. 1, 2002, to Metzger et al., the disclosure of which is hereby incorporated by reference in its entirety.

Figure 4A:
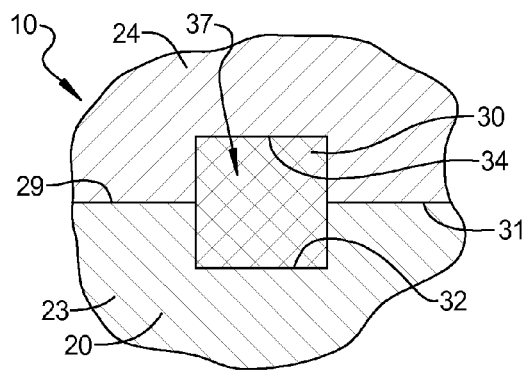
FIG. 4A is a section view of a resorbing member of the prosthetic device of FIG. 1.

As shown in FIGS. 3 and 4A, the resorbing member 30 can have a block-like, or any other suitable shape. Also, the superior surface 29 of the tray 23 can include an opening 32 (e.g., a recess), and the inferior surface 31 of the bearing 24 can include a similar opening 34 (e.g., a recess). The openings 32, 34 can align when the bearing 24 is supported on the tray 23, and the resorbing member 30 can be received in both openings 32, 34 (FIG. 4A). In some embodiments represented in FIG. 3, the resorbing members 30 can be disposed anteriorly and posteriorly from the guide post 33. However, it will be appreciated that the resorbing members 30 can be disposed at any suitable position in the prosthetic device 10.

Moreover, in some embodiments, the resorbing members 30 can be inserted between the bearing 24 and the second prosthetic member 20 during surgery, while the prosthetic device 10 is being implanted. In other embodiments, the resorbing member 30 can be made of a liquid material that can be injected with a needle (not shown) between the bearing 24 and the second prosthetic member 20, and the resorbing member 30 can subsequently harden and cure into a solid state to limit the bearing 24 against movement relative to the prosthetic member 20.

As shown in FIGS. 3 and 4A, the size and shape of the resorbing member 30 substantially matches the combined size and shape of the openings 32, 34. Thus, the resorbing member 30 can substantially fill the openings 32, 34, and the resorbing member 30 can substantially fix the bearing 24 against movement relative to the second prosthetic member 20. For instance, the resorbing member 30 can fix the bearing 24 against linear movement in the anterior-posterior direction as represented by the vertical, double-headed arrow in FIG. 3. Also, the resorbing member 30 can fix the bearing 24 against rotational movement about the guide post 33 as represented by the curved, double-headed arrow in FIG. 3.

Figure 4B:
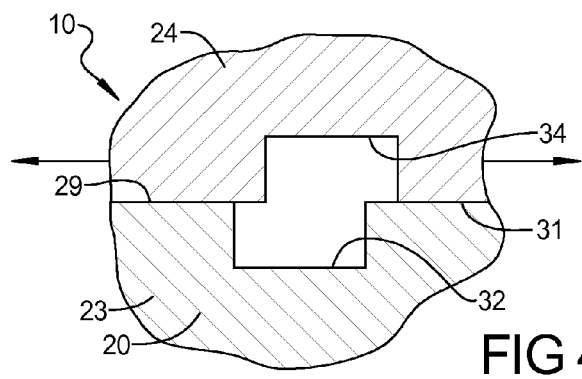
FIG. 4B is a section view of the prosthetic device of FIG. 4A after the resorbing member has resorbed.

Then, as shown in FIG. 4B, the resorbing member 30 can resorb, leaving the bearing 24 free to move relative to the second prosthetic member 20 in an increased range of movement. In some embodiments, once the resorbing member 30 resorbs, the bearing 24 can move in a linear, anterior-posterior range of movement as represented by the vertical, double-headed arrow in FIG. 3. Also, in some embodiments, once the resorbing member 30 resorbs, the bearing 24 can rotate about the guide post 33 as represented by the curved, double-headed arrow in FIG. 3. However, it will be appreciated that the prosthetic device 10 can be configured such that the bearing 24 moves in any direction and within any range of movement relative to the second prosthetic member 20 once the resorbing member 30 resorbs.

Furthermore, in some embodiments, the resorbing member 30 can automatically resorb over time. In other embodiments, the resorbing member 30 can selectively resorb at a predetermined time. In the latter case, a surgeon can inject a substance into the patient, which causes the resorbing member 30 to begin to resorb. More specifically, the resorbing member 30 can be made from or include a magnesium alloy, and the surgeon can inject a saline buffer that sets off resorption. Furthermore, the resorbing member 30 can be made from or include calcium phosphate or calcium carbonate, and a citric acid can be injected to resorb and dissolve the resorbing member 30 relatively quickly.

Figure 5A:
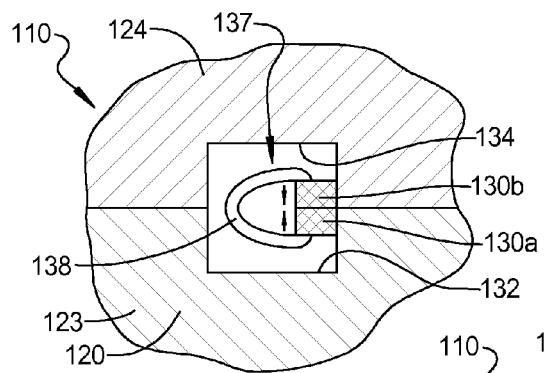
FIG. 5A is a section view of another exemplary embodiment of a resorbing member of the prosthetic device of FIG. 1.
Figure 5B:
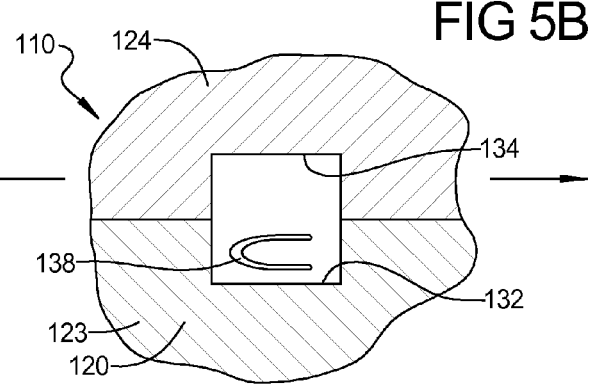
FIG. 5B is a section view of the prosthetic device of FIG. 5A after the resorbing member has resorbed.

Referring now to FIGS. 5A and 5B, further exemplary embodiments of the prosthetic device 110 are illustrated. Components that are similar to those of the embodiments of FIGS. 1-4B are indicated with similar reference numbers, increased by 100.

As shown in FIG. 5A, the prosthetic device 110 can include a first resorbing member 130a and a second resorbing member 130b. The first resorbing member 130a can be fixed to the tray 123 and can project into the opening 132. Likewise, the second resorbing member 130b can be fixed to the bearing 124 and can project into the opening 134. When the bearing 124 is supported on the tray 123, the first and second resorbing members 130a, 130b can abut against each other.

The prosthetic device 110 can also include a biasing member 138. The biasing member 138 can couple the bearing 124 and the second prosthetic member 120 to limit relative movement as discussed above. Also, the biasing member 138 can be biased to allow increased relative movement between the bearing 124 and the second prosthetic member 120 once the resorbing members 130a, 130b resorb.

The biasing member 138 can be of any suitable type, such as a compression spring. As shown in the exemplary embodiments illustrated, the biasing member 138 can be a resilient C-shaped clip. The biasing member 138 can engage the first and second resorbing members 130a, 130b and compress the first and second resorbing members 130a, 130b toward each other. As such, the biasing member 138 can bias the bearing 124 toward the second prosthetic member 120 to limit movement of the bearing 124 relative to the second prosthetic member 120.

Then, as shown in FIG. 5B, the resorbing members 130a, 130b can resorb, allowing the biasing member 138 to move into one of the openings 132, 134. For instance, as shown in FIG. 5B, the biasing member 138 can move completely into the opening 132 and out of the opening 134. This can allow the bearing 124 to move relative to the second prosthetic member 120 as discussed above. In some embodiments, the biasing member 138 can be tethered or otherwise attached to either the bearing 124 or the second prosthetic member 120 so that the biasing member 138 is retained within either the opening 132 or the opening 134, respectively, after resorption. Also, in some embodiments, the biasing member 138 can be removed from the openings 132, 134 by a surgeon after resorption of the members 130a, 130b. Also, in some embodiments, the biasing member 138 itself can be made of resorbable material.

Figure 6A:
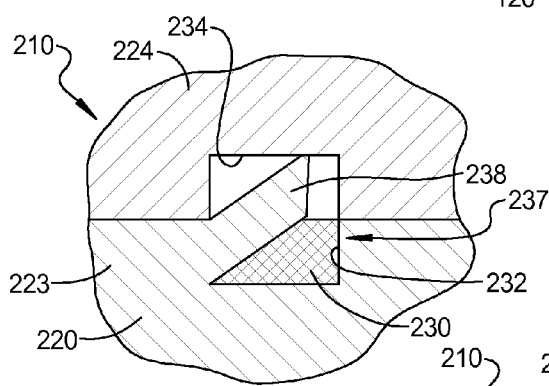
FIG. 6A is a section view of another exemplary embodiment of a resorbing member of the prosthetic device of FIG. 1.
Figure 6B:
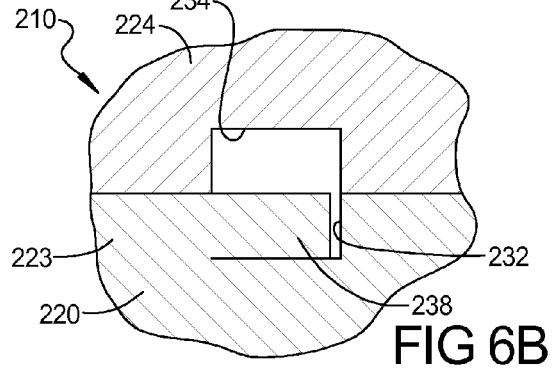
FIG. 6B is a section view of the prosthetic device of FIG. 6A after the resorbing member has resorbed.

Referring now to FIGS. 6A and 6B, further exemplary embodiments of the prosthetic device 210 are illustrated. Components that are similar to those of the embodiments of FIGS. 5A and 5B are indicated with similar reference numbers, increased by 100.

As shown in FIG. 6A, the biasing member 238 can be a tab that is fixed to the tray 223. The biasing member 238 can resiliently bend in a superior direction toward the bearing 224 to be received within the opening 234. Also, the resorbing member 230 can be wedged between the biasing member 238 and the tray 223 to thereby push the biasing member 238 and hold the biasing member 238 within the opening 234. As such, the biasing member 238 can engage the bearing 224 to limit movement of the bearing 224 relative to the second prosthetic member 220.

Then, as shown in FIG. 6B, when the resorbing member 230 resorbs, the biasing member 238 can resiliently recover to move back into the opening 232 of the second prosthetic member 220. Thus, the bearing 224 can move relative to the second prosthetic member 220 as discussed above.

It will be appreciated that the biasing member 238 could be fixed to the bearing 224, and the resorbing member 230 could push the biasing member 238 into the opening 232 of the second prosthetic member 220 without departing from the scope of the present disclosure.

Furthermore, in the embodiments of FIGS. 6A and 6B, the biasing member 238 is smaller than the opening 234. As such, the bearing 224 can move relative to the second prosthetic member 220 over a first range of movement even when the biasing member 238 is within the opening 234. However, once the resorbing member 230 resorbs, the biasing member 238 can move out of the opening 234, and the bearing 224 can move within a comparatively larger second range of movement relative to the second prosthetic member 220.

Figure 7:
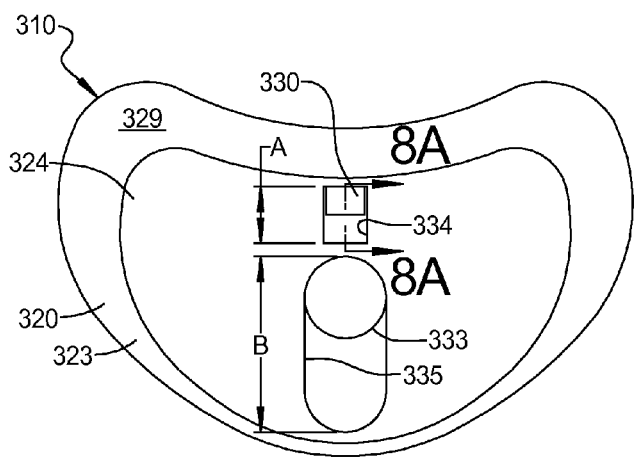
FIG. 7 is a top view of another exemplary embodiment of a resorbing member of the prosthetic device of FIG. 1.
Figure 8A:
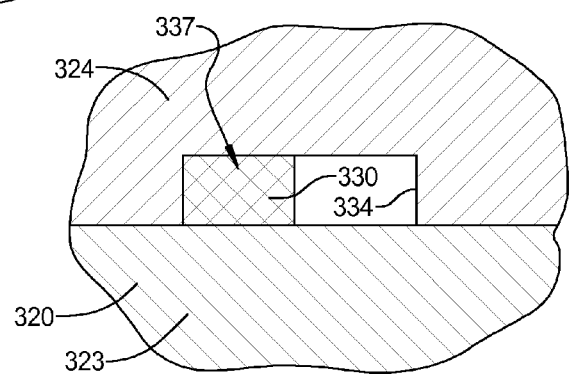
FIG. 8A is a section view of the resorbing member of the prosthetic device of FIG. 7.
Figure 8B:
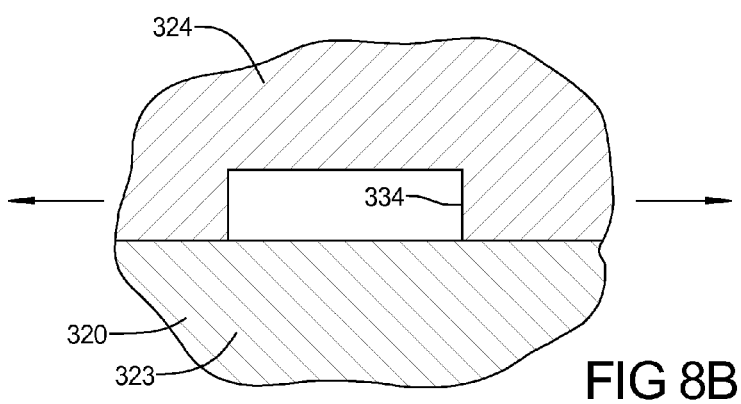
FIG. 8B is a section view of the prosthetic device of FIG. 7A after the resorbing member has resorbed.

Referring now to FIGS. 7-8B, further exemplary embodiments of the prosthetic device 310 are illustrated. Components that are similar to those of the embodiments of FIGS. 1-4B are indicated with similar reference numbers, increased by 300.

As shown, the opening 334 (e.g., recess) of the bearing 324 can be a slot that extends in the posterior-anterior direction as represented by the vertical, double headed arrow in FIG. 7. Moreover, the through hole 335 of the bearing 324 can be a slot that extends in the posterior-anterior direction. The through hole 335 can be longer than the opening 334.

Also, as shown in FIG. 8A, the resorbing member 330 can be fixed to tray 323. The resorbing member 330 can project away from the tray 323 to be received in the opening 334. The resorbing member 330 can be smaller than the opening 334. As such, the resorbing member 330 can limit movement of the bearing 324 relative to the tray 323 to within a first range A of linear movement in the posterior-anterior direction, and rotation of the bearing 324 relative to the tray 323 can be substantially eliminated by the resorbing member 330 as shown in FIG. 7. Thus, a first degree of freedom is present (i.e., anterior-posterior movement) and a second degree of freedom (i.e., rotation) is restrained. However, as shown in FIG. 8B, once the resorbing member 330 resorbs, the bearing 324 can move relative to the tray 323 over a larger range of motion. More specifically, the resorbing member 330 no longer limits movement of the bearing 324, and the bearing 324 can move relative to the tray 323 within a second range B of linear movement (FIG. 7) in the posterior-anterior direction. Also, the bearing 324 can also rotate about the guide post 333 once the resorbing member 330 resorbs. As such, the bearing 324 has multiple degrees of freedom (i.e., anterior-posterior and rotational movement). Furthermore, abutment between the guide post 333 and the through hole 335 can limit anterior-posterior and rotational movement of the bearing 324 relative to the tray 323.

Similarly, as shown in FIG. 9, the through hole 434 in the bearing 424 can be substantially the same size as the guide post 430. Also, the through hole 434 in the bearing 424 can be a slot that curves about the axis of the guide post 430. Furthermore, the tray 423 can include a projection 450 that extends in a superior direction to be received in the through hole 434. The projection 450 can be wedge shaped. Also, resorbing members 430a, 430b can be fixed to opposite sides of the projection 450. As such, abutment between the resorbing members 430a, 430b and the inner surface of the through hole 434 can limit rotational movement of the bearing 424 about the guide post 430 within a first rotational range of motion A'. However, once the resorbing members 430a, 430b resorb, abutment between the projection 450 and the inner surface of the through hole 434 can limit rotational movement of the bearing 424 about the guide post 430 within a larger second rotational range of motion B'.

It will be appreciated that in the embodiments of FIGS. 7-9, the resorbing members 330, 430a, 430b could be fixed to the bearing 324, 424. As such, the second prosthetic members 320, 420 could receive the resorbing members 330, 430a, 430b in order to limit the relative movement of the bearing 324, 424 and the second prosthetic members 320, 420 within the first range of motion A, A'.

Referring now to FIG. 10, further exemplary embodiments of the prosthetic device 510 are illustrated. Components that are similar to those of the embodiments of FIGS. 1-4B are indicated with similar reference numbers, increased by 500.

As shown, the bearing 524 can include a base post 552 that extends in an inferior direction to be received in an opening 554 of the second prosthetic member 520. The base post 552 and the opening 554 can both be tapered and can have a substantially similar size. Furthermore, the base post 552 can include a through hole 558 that extends transverse to the axis C. Likewise the post 525 of the second prosthetic member 520 can include a through hole 556 that aligns with the through hole 558.

The resorbing member 530 can be received in both through holes 556, 558 to substantially fix the bearing 524 against rotation about the axis C relative to the second prosthetic member 520. Thus, the resorbing member 530 can be considered a resorbable fastener. Once the resorbing member 530 resorbs, the bearing 524 can rotate about the axis C relative to the second prosthetic member 520. Accordingly, the initial, first range of movement of the bearing 524 relative to the second prosthetic member 520 can be substantially equal to zero, and the eventual, second range of movement of the bearing 524 relative to the second prosthetic member 520 can be greater than zero.

In other embodiments, the resorbing member 530 can initially fix the bearing 524 to the second prosthetic member 520. Over time, the resorbing member 530 can only partially resorb, and at a certain time after resorption, the resorbing member 530 can weaken and fracture due to forces transferred between the bearing 524 and the second prosthetic member 520. Once the resorbing member 530 fractures, the bearing 524 and the second prosthetic member 520 can move relative to each other over the second range of movement.

It will be appreciated that the resorbing member 30-530 can limit movement of only a portion of the bearing 24-524 relative to the second prosthetic member 20-520. As such, after resorbing, that portion of the bearing 24-524 can move relative to the second prosthetic member 20-520 while other portions of the bearing 24-524 remain limited against such relative movement.

Furthermore, as discussed above, the resorbing member 30-530 can initially (e.g., immediately after implantation) limit movement of the bearing 24-524 relative to the second prosthetic member 20-520. The resorbing member 30-530 can fix the bearing 24-524 to the second prosthetic member 20-520 or can allow relative movement within a first range of movement. Limiting movement in this way can promote healing of soft tissue, etc. Eventually (e.g., well after surgery and after healing has occurred) the resorbing member 30-530 can resorb, thereby allowing the bearing 24-524 to move relative to the second prosthetic member 20-520 over a larger, second range of movement without the need for surgical intervention. This can allow for improved mobility of the joint 14.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A prosthetic device for an anatomical feature comprising:
 a prosthetic member configured to be attached to the anatomical feature;
 a bearing having a bearing surface configured to support an articulating surface for articulation thereon; and
 a bearing restraining member that controls movement of the bearing relative to the prosthetic member to allow a first degree of freedom and restrain a second degree of freedom at a first time and to allow the first degree of freedom and allow the second degree of freedom at a second time, wherein at least one of the prosthetic member and the bearing defines an opening that receives the bearing restraining member.

2. The prosthetic device of claim 1, wherein the bearing restraining member includes a resorbable member that resorbs to allow for increased movement of the bearing relative to the prosthetic member at the second time.

3. The prosthetic device of claim 1, wherein the bearing restraining member is fixed to the prosthetic member and extends away from the prosthetic member into the opening in the bearing.

4. The prosthetic device of claim 1, wherein the first degree of freedom is anterior-posterior movement of the bearing relative to the prosthetic member and the second degree of freedom is rotation of the bearing relative to the prosthetic member.

5. The prosthetic device of claim 4, wherein at the first time, the bearing restraining member limits the anterior-posterior movement to a first range of linear movement and at the second time limits the anterior-posterior movement to a second range of linear movement, where the second range of linear movement is greater than the first range of linear movement.

6. The prosthetic device of claim 1, wherein the prosthetic member is a tibial prosthetic member having a superiorly extending guide post and the bearing defines a through hole configured to receive the superiorly extending guide post of the tibial prosthetic member.

7. The prosthetic device of claim 6, further comprising:
 a femoral prosthetic member having the articulating surface for articulating on the bearing surface of the bearing.

8. The prosthetic device claim 6, wherein the bearing defines an elongated slot and the bearing restraining member extends from the tibial prosthetic member into the elongated slot.

9. A prosthetic device for an anatomical feature comprising:
 a tibial prosthetic member having a tibial tray and a guide post extending from the tibial tray;
 a bearing having a bearing surface configured to support an articulating surface for articulation thereon, the bearing defining an elongated bore extending along a longitudinal axis and configured to receive the guide post and defining an elongated opening extending along the longitudinal axis; and
 a bearing restraining member extending into the elongated opening to control movement of the bearing relative to the tibial prosthetic member at a first time and a second time, wherein movement at the first time is different than the movement at the second time.

10. The prosthetic device of claim 9, wherein the bearing restraining member includes a resorbable member that resorbs to allow for increased movement of the bearing relative to the tibial prosthetic member at the second time.

11. The prosthetic device of claim 9, wherein at the first time, the bearing restraining member allows a first range of linear movement and restrains rotational movement of the bearing relative to the tibial prosthetic member and at the second time, the bearing restraining member allows a second range of linear movement and allows rotational movement of the bearing relative to the tibial prosthetic member, the second linear range being larger than the first linear range.

12. The prosthetic device of claim 9, wherein the bearing restraining member allows for increased movement of the bearing in a substantially anterior-posterior direction relative to the tibial prosthetic member at the second time.

13. The prosthetic device of claim 9, wherein the bearing restraining member allows for increased rotational movement of the bearing relative to the tibial prosthetic member at the second time.

14. The prosthetic device of claim 9, further comprising:
 a femoral prosthetic member having the articulating surface for articulating on the bearing surface of the bearing.

15. A prosthetic device for an anatomical feature comprising:
 a femoral prosthetic member configured to be attached to a femur and having an articulating surface;
 a tibial prosthetic member configured to be attached to a tibia;
 a bearing having a bearing surface configured to support the articulating surface of the femoral prosthetic member for articulation thereon; and
 a bearing restraining member that controls movement of the bearing relative to the tibial prosthetic member, wherein the bearing restraining member allows only a first degree of freedom of movement at a first time and allows a first and a second degree of freedom of movement at a second time.

16. The prosthetic device of claim 15, wherein the bearing restraining member includes, a resorbable member that resorbs to allow for increased movement of the bearing relative to the tibial prosthetic member at the second time.

17. The prosthetic device of claim 15, wherein the first degree of freedom of movement is linear movement and the second degree of freedom of movement is rotational movement.

18. The prosthetic device of claim 17, wherein at the first time, linear movement is controlled to a first range and at the second time, linear movement is controlled to a second range, wherein the second range is larger than the first range.

19. The prosthetic device of claim 15, wherein the bearing restraining member is fixed to the tibial prosthetic member and extends away from the tibial prosthetic member into a recess in the bearing.

* * * * *